US010830712B2

(12) United States Patent
Butani et al.

(10) Patent No.: US 10,830,712 B2
(45) Date of Patent: Nov. 10, 2020

(54) SYSTEM AND METHOD FOR CABINET X-RAY SYSTEMS WITH CAMERA

(71) Applicant: KUB Technologies, Inc., Stratford, CT (US)

(72) Inventors: Vikram Butani, Stratford, CT (US); Yan Chen, Stratford, CT (US); Edwin Divakaran Maria-Selvaraj, Stratford, CT (US); Chester Lowe, Stratford, CT (US); Roberto Velasco, Stratford, CT (US)

(73) Assignee: Kub Technologies, Inc., Stratford, CT (US)

( * ) Notice: Subject to any disclaimer, the term of this patent is extended or adjusted under 35 U.S.C. 154(b) by 46 days.

(21) Appl. No.: 15/935,358

(22) Filed: Mar. 26, 2018

(65) Prior Publication Data

US 2018/0275076 A1    Sep. 27, 2018

Related U.S. Application Data

(60) Provisional application No. 62/476,984, filed on Mar. 27, 2017.

(51) Int. Cl.
*G01N 23/044* (2018.01)
*G06T 11/00* (2006.01)
(Continued)

(52) U.S. Cl.
CPC ............ *G01N 23/044* (2018.02); *A61B 6/02* (2013.01); *A61B 6/025* (2013.01); *A61B 6/42* (2013.01); *A61B 6/4208* (2013.01); *A61B 6/4258* (2013.01); *A61B 6/44* (2013.01); *A61B 6/4417* (2013.01); *A61B 6/4429* (2013.01); *A61B 6/4435* (2013.01); *A61B 6/4452* (2013.01); *A61B 6/4458* (2013.01); *A61B 6/4464* (2013.01); *A61B 6/502* (2013.01); *A61B 6/508* (2013.01); *G01N 23/04* (2013.01);
(Continued)

(58) Field of Classification Search
CPC .. A61B 6/02; A61B 6/025; A61B 6/44; A61B 6/4429; A61B 6/4452; A61B 6/508; A61B 6/4458; G01N 23/044
USPC .......................... 378/21–26, 62, 63, 196, 197
See application file for complete search history.

(56) References Cited

U.S. PATENT DOCUMENTS

| 5,872,828 A * | 2/1999 | Niklason | ................ A61B 6/025 378/23 |
| 6,633,626 B2 * | 10/2003 | Trotter | ..................... A61B 6/00 378/37 |

(Continued)

*Primary Examiner* — Allen C. Ho
(74) *Attorney, Agent, or Firm* — Ziegler IP Law Group, LLC

(57) ABSTRACT

The present disclosure relates to the field of a cabinet x-ray incorporating an x-ray tube, an x-ray detector, and a real-time camera, either high definition or standard resolution, for the production of organic and non-organic images. The computing device can receive video data from the camera and the x-ray detector and determines, based on the video data, an overlay of the captured x-ray image with the captured real-time image or display images adjacently i.e. Picture-In-Picture (PIP). In particular, the disclosure relates to a system and method with corresponding apparatus for capturing a real-time image simultaneously with the x-ray image allowing a cabinet x-ray unit to attain and optimize images with exact orientation of the 2 images.

26 Claims, 10 Drawing Sheets

View in Sample Chamber with Door Open with X-ray source at position (14) Top Center

(51) Int. Cl.
*A61B 6/00* (2006.01)
*A61B 6/02* (2006.01)
*G01N 23/04* (2018.01)

(52) U.S. Cl.
CPC ...... *G06T 11/006* (2013.01); *G01N 2223/401* (2013.01); *G01N 2223/612* (2013.01); *G01N 2223/6123* (2013.01); *G01N 2223/6126* (2013.01); *G06T 2210/41* (2013.01)

(56) References Cited

U.S. PATENT DOCUMENTS

| | | | |
|---|---|---|---|
| 6,707,878 B2* | 3/2004 | Claus | G06T 11/005 378/210 |
| 6,748,047 B2* | 6/2004 | Gonzalez Trotter | G01N 23/046 378/62 |
| 7,218,766 B2* | 5/2007 | Eberhard | A61B 6/463 128/922 |
| 7,708,462 B2* | 5/2010 | Fujiwara | A61B 6/025 378/206 |
| 7,760,924 B2* | 7/2010 | Ruth | G06T 11/006 382/128 |
| 8,326,012 B2* | 12/2012 | Kreeger | G16H 50/50 382/132 |
| 8,547,402 B2* | 10/2013 | Kreeger | G16H 50/50 345/634 |
| 9,113,796 B2* | 8/2015 | Engel | A61B 6/025 |
| 9,138,193 B2* | 9/2015 | Lowe | A61B 6/502 |
| 9,386,956 B2* | 7/2016 | Lee | G06T 11/006 |
| 9,392,989 B2* | 7/2016 | Dornberger | A61B 6/0414 |
| 9,675,277 B2* | 6/2017 | Arai | A61B 5/1075 |
| 9,949,699 B2* | 4/2018 | Visser | G06T 11/003 |
| 10,646,178 B2* | 5/2020 | Butani | A61B 6/488 |
| 10,652,990 B2* | 5/2020 | Butani | H05G 1/06 |
| 10,670,545 B2* | 6/2020 | Butani | G01N 23/044 |
| 2015/0131773 A1 | 5/2015 | Lowe et al. | |

* cited by examiner

FRONT VIEW INTO CABINET
Door Open

Typical Example of an X-ray Cabinet System

View in Sample Chamber with Door Open with
X-ray source at position (14) Top Center

**Lateral View of X-Ray Source
Mounted to Swing Arm at position (14)

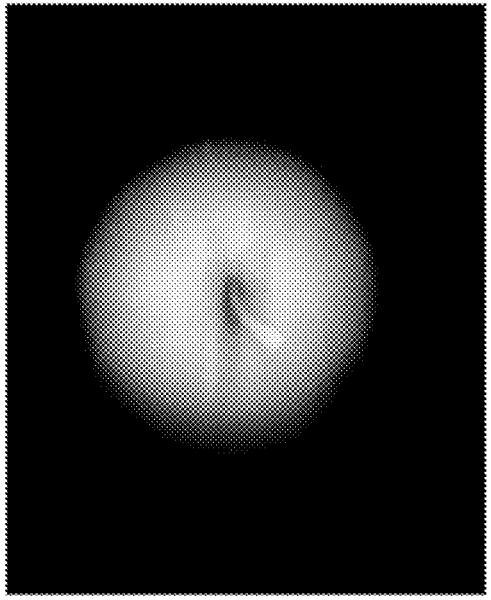
Fig. 7A - Top Slice – 59m
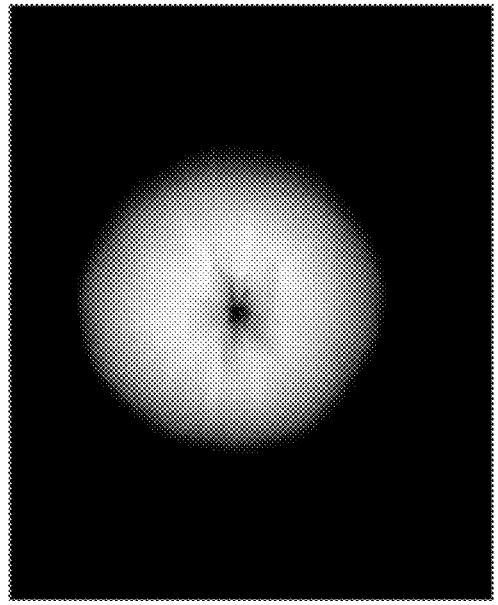
Fig. 7B - Bottom Slice – 13.5 mm
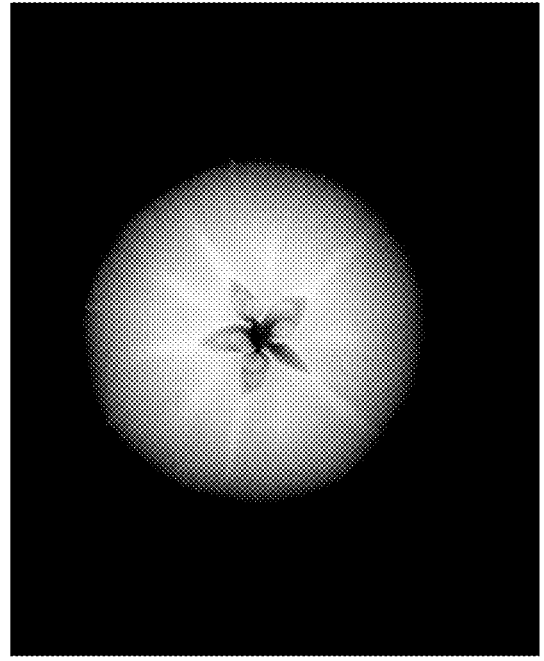
Fig. 7C - Middle Slice – 30.5 mm

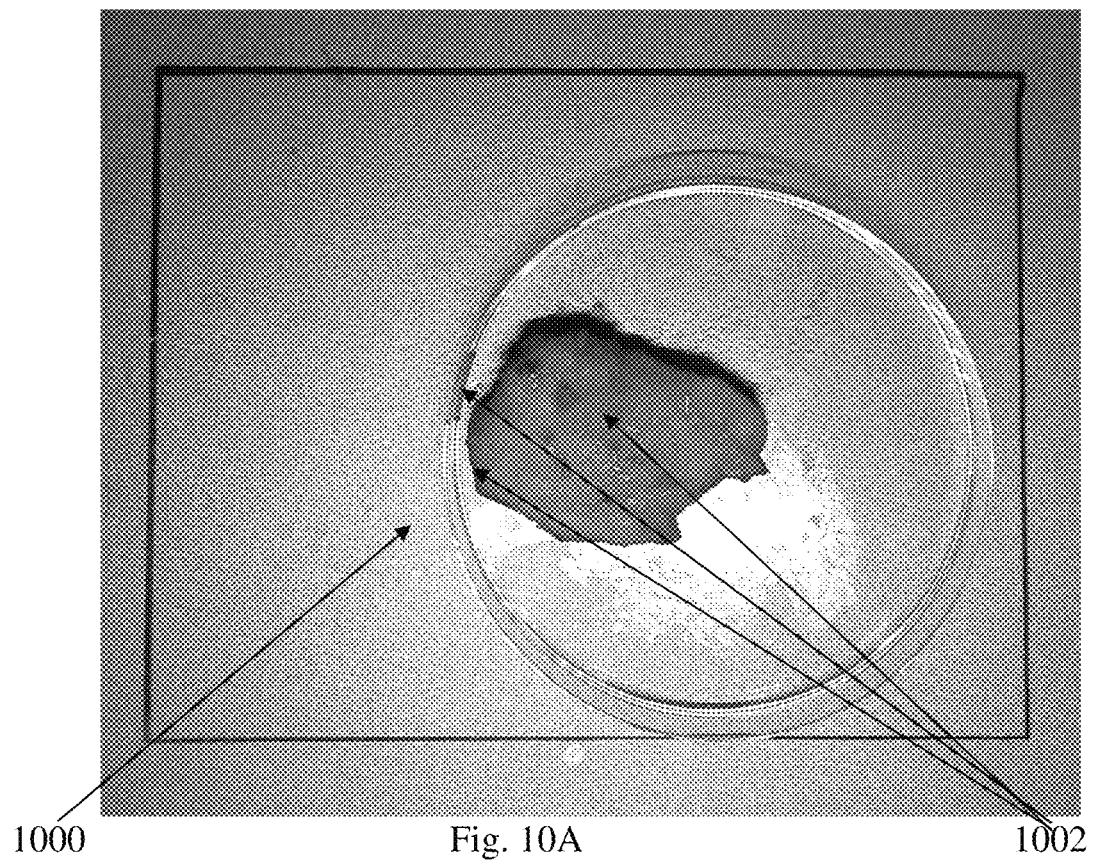
1000  Fig. 10A  1002
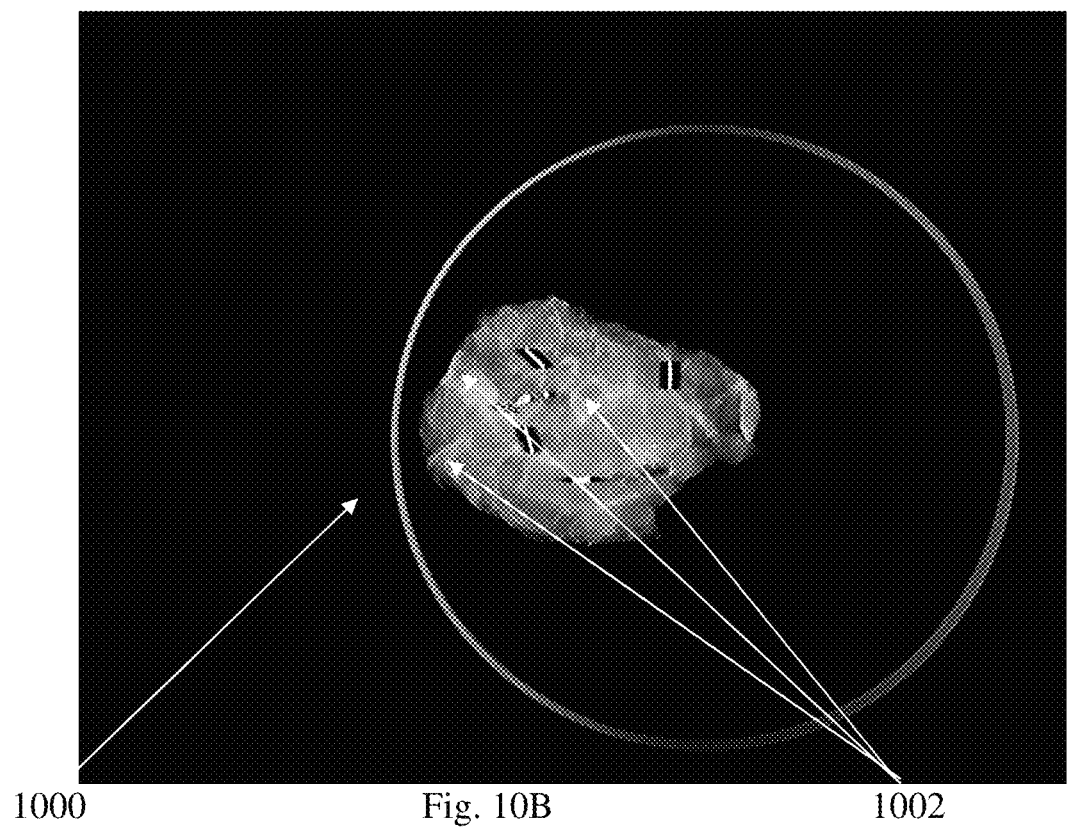
1000  Fig. 10B  1002

SYSTEM AND METHOD FOR CABINET X-RAY SYSTEMS WITH CAMERA

CROSS-REFERENCE TO RELATED APPLICATIONS

This application claims priority to and the benefit of U.S. Provisional Patent Application Ser. No. 62/476,984 filed Mar. 27, 2017, the disclosure of which is incorporated herein by reference in its entirety.

BACKGROUND

Field of the Present Disclosure

The present disclosure relates to the field of a cabinet x-ray incorporating a system and method for incorporating a camera, either high definition or standard resolution, taking an optical image and an x-ray image and displaying the resulting images.

Background

Today, conventional breast specimen systems can gather a digital breast specimen radiogram and an optical image separately. In these systems, the radiograms and optical images of a tissue or bone specimen can be viewed separately for analysis.

With a unit incorporating a camera, the clinician can utilize the resultant photo or optical image to expeditiously visualize the specimen excised from the patient to confirm orientation of the excised sample saving time for both the patient on the treatment table and the clinician.

It would be advantageous in breast procedure rooms to allow the medical professional to operate the cabinet x-ray unit to analyse the excised breast tissue or specimen utilizing the unit to capture both an x-ray image and an optical image of the sample for informational and/or diagnostic purposes. As a result, a clinician or physician could view the 2 images in the same and exact orientation and display them, for example, separately, side-by-side, picture-in-picture (PIP) or overlaid upon each other.

Specimen radiography is considered the most cost-effective screening method for the detection of breast cancer in surgically removed breast tissue. However, the sensitivity of specimen radiography is often limited by the presence of overlapping dense fibroglandular tissue in the breast specimen. Dense parenchyma reduces the conspicuity of abnormalities and thus constitutes one of the main causes of missed breast cancer diagnosis. The advent of full-field digital detectors offers opportunities to develop advanced techniques for improved imaging of dense breasts, such as digital tomosynthesis.

SUMMARY

The present disclosure relates to the field of a cabinet x-ray incorporating an x-ray tube, an x-ray detector, and a real-time camera for the production of organic and non-organic specimen images. The computing device receives video data from the real-time camera and the x-ray detector and determines the orientation of the specimen, based on the video data, an overlay of the captured x-ray image with the captured real-time image or display an adjacent image i.e. Picture-In-Picture (PIP). This facilitates and aids the surgeon/user in ensuring that the proper amount of tissue has been excised. In particular, the disclosure relates to a system and method with corresponding apparatus for capturing a real-time image simultaneously with the x-ray image allowing a cabinet x-ray unit to attain and optimize images with substantially the same, preferably the exact, orientation of the 2 images.

In one embodiment, the aspects of the present disclosure are directed to a system and method including a cabinet x-ray system incorporating a real-time camera. This embodiment includes a cabinet x-ray system, a base unit including an image processor and a display, an imaging chain incorporated into the base unit, including an x-ray source with x-ray detector, a system configured to receive video data and an interface for enabling an analog/digital signal to be transferred from an image capture apparatus to the image processor of the base unit. The system may be further be configured to supply standard or high-definition (HD) real-time images. A camera can be used to receive video data and may be digital to provide electronic images. The cabinet x-ray system may concurrently capture an x-ray image and a real-time image. The camera may be mounted onto the system so as to integrate an exact capture/orientation image of the sample being x-rayed. The unit may be enclosed in a cabinet x-ray system. The unit may be utilized for excised tissue, organ or bone specimens. The unit may be utilized for any organic or inorganic specimen that fits inside the system framework or x-ray cabinet. The image capturing mechanism may be mounted in a cabinet x-ray system, such as the cabinet system illustrated in the embodiment shown in FIG. 1. The real-time image can be displayed or overlaid onto the x-ray image or adjacent to the x-ray image (Picture-in-Picture—PIP). The system may be utilized on two-dimensional (2-D) and three-dimensional (3-D) tomographic radiographs.

In another embodiment, the aspects of the present disclosure are directed to a computing device including at least with one processor and at least one display unit operable by the at least one processor. The at least one display unit operable by the at least one processor is configured to output, for display, determining, based on the video data, a display action and be responsive to determining the preference/initiated action, output for display the resultant images attained by the x-ray cabinet system.

In another embodiment, the aspects of the present disclosure are directed to a cabinet x-ray and optical camera system for obtaining x-ray images and optical images of a specimen. The cabinet x-ray and optical camera system includes a cabinet defining an interior chamber, a display, an x-ray system, an optical camera and a controller. The x-ray system includes an x-ray source, an x-ray detector and a specimen platform. The optical camera is configured to capture an optical image of the specimen. The controller is configured to selectively energize the x-ray source to emit x-rays through the specimen to the x-ray detector, control the x-ray detector to collect a projection x-ray image of the specimen when the x-ray source is energized, selectively display the x-ray image on the display, control the optical camera to capture and collect the optical image of the specimen and selectively display the optical image on the display.

In another embodiment, the aspects of the present disclosure are directed to a cabinet x-ray and optical camera system for obtaining x-ray images, projection x-ray images, reconstructed tomosynthetic x-ray images and optical images of a specimen. The cabinet x-ray and optical camera system includes a cabinet defining an interior chamber and an equipment enclosure, a display, an x-ray system, an optical camera and a controller. The x-ray system includes an x-ray source positioned in the interior chamber, an x-ray detector positioned in the interior chamber, a specimen platform positioned in the interior chamber and which is a protective cover of and in physical contact with the x-ray detector and a motion control mechanism positioned in the interior chamber and configured for moving the x-ray source to or along a plurality of positions within the interior chamber relative to the specimen disposed on the specimen platform. The optical camera is positioned in the interior chamber and configured to capture an optical image of the specimen. The controller is positioned in the equipment enclosure and configured to selectively energize the x-ray source to emit x-rays through the specimen to the x-ray detector at selected positions of the x-ray source relative to the specimen such that the isocenter of the emitted x-rays at the selected positions is located at a surface of the x-ray detector, control the x-ray detector to collect projection x-ray images of the specimen when the x-ray source is energized at the selected positions, wherein one of the projection x-ray images is a two-dimensional x-ray image taken at standard imaging angle of approximately 0°, create a tomosynthetic x-ray image reconstructed from a collection of projection x-ray images, process the collection of the projection x-ray images in the controller into one or more reconstructed tomosynthetic x-ray images representing a volume of the specimen and relating to one or more image planes that are selectively the same or different from that of the two-dimensional x-ray image, control the optical camera to capture and collect the optical image of the specimen and selectively display at least one of the two-dimensional x-ray image, the one or more reconstructed tomosynthetic x-ray images and the optical image on the display.

In another embodiment, the aspects of the present disclosure are directed to a method for obtaining an x-ray image and an optical image of a specimen in a cabinet x-ray and optical image system, processing and displaying the x-ray image and optical image of the specimen. The cabinet x-ray and optical image system includes a cabinet defining an interior chamber, a display, an x-ray system, and optical camera and a controller. The x-ray system includes an x-ray source, an x-ray detector and a specimen platform. The optical camera is configured to capture an optical image of the specimen. The controller is configured to selectively energize the x-ray source to emit x-rays through the specimen to the x-ray detector, control the x-ray detector to collect a projection x-ray image of the specimen when the x-ray source is energized, selectively display the x-ray image on the display, control the optical camera to capture and collect the optical image of the specimen and selectively display the optical image on the display. The method includes controlling the x-ray detector to collect an x-ray image of the specimen when the x-ray source is energized, controlling the optical camera to capture and collect the optical image of the specimen and selectively displaying at least one of the x-ray image and the optical image on the display.

BRIEF DESCRIPTION OF THE DRAWINGS

To further clarify the above and other advantages and features of the present disclosure, a more particular description of the disclosure will be rendered by reference to specific embodiments thereof that are illustrated in the appended drawings. It is appreciated that these drawings depict only typical embodiments of the disclosure and are therefore not to be considered limiting of its scope. The disclosure will be described and explained with additional specificity and detail through the use of the accompanying drawings in which:

FIGS. 7A, 7B and 7C—Displays the results of the imaging of an apple at multiple depth cuts after tomosynthesis reconstruction in a cabinet X-ray system incorporating aspects of the present disclosure.

FIGS. 10A and 10B—display an HD view and a radiographic image of a breast specimen utilizing exemplified embodiments of the present disclosure;

DETAILED DESCRIPTION

Figure 1:
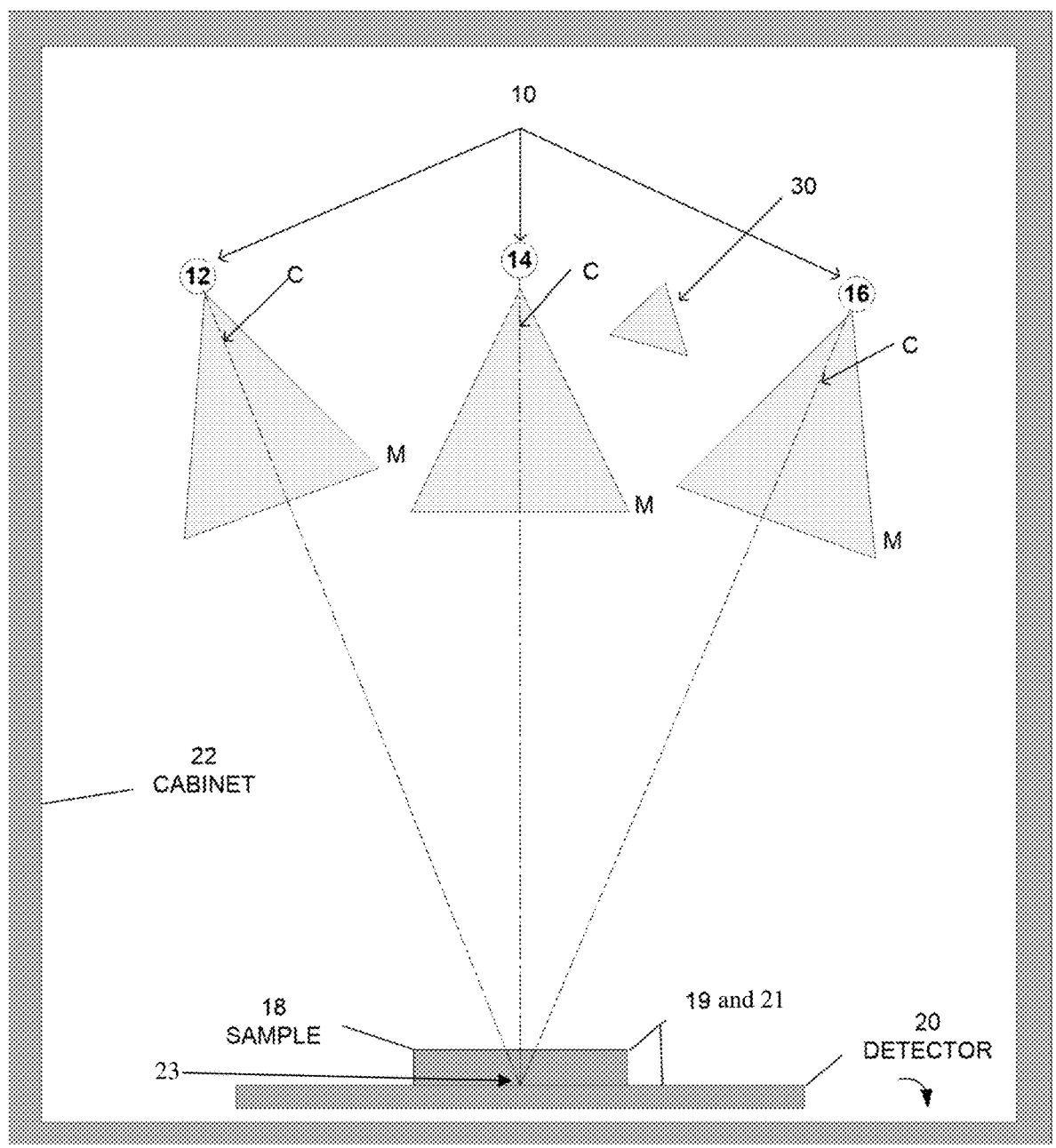
FIG. 1—Schematically illustrates a front view of an X-ray source, a specimen/sample, and a digital detector, where the X-ray source moves relative to the specimen for imaging the specimen at different angles, in one embodiment of a system incorporating aspects of the present disclosure.

In general, aspects of this disclosure include a device (cabinet x-ray system) utilizing a camera to capture an optical image (in black and white, gray scale or color, preferably color), preferably in real-time, of a sample or specimen also being x-rayed to produce an x-ray image, preferably with the resulting 2 images being at substantially or, preferably exactly, the same orientation. The x-ray image can include a two-dimensional (2-D) x-ray image or a synthetic x-ray image assembled from more than one x-ray image (e.g., a tomosynthetic image).

The photo/captured camera optical image, preferably in real-time, may be displayed on the monitor either overlaid onto the resultant x-ray image or synthetic x-ray image assembled from more than one x-ray image (e.g., a tomosynthetic image) of the sample or as back to back viewing on a monitor between two images or a side-by-side or Picture-In-a-Picture (PIP) displayed adjacent to the x-ray image or synthetic x-ray image of the sample. A device capturing both an x-ray image and an optical image, the latter preferably in real-time, of the specimen facilitates confirmation and orientation for the clinician to verify margins and other specimen features are achieved by the professional after it is removed from a patient.

A preferred embodiment system would be to incorporate an HD (high-definition) optical camera into a cabinet x-ray unit allowing the system to capture an HD optical image and x-ray image of the specimen where the images so obtained can be displayed as disclosed herein.

The present disclosure and embodiments included therein can relate to specimen radiography but the disclosure is not isolated to specimen radiography but may be utilized, for example, for non-destructive testing, pathology as well as any radiographic analysis of organic and non-organic samples or specimens, requiring a cabinet x-ray system but is not limited to just an HD camera but to any camera fitting within the confines of the cabinet x-ray system.

Reference will now be made to figures wherein like structures will be provided with like reference designations. It is understood that the drawings are diagrammatic and schematic representations of exemplary embodiments of the disclosure and are not limiting of the present disclosure nor are they necessarily drawn to scale. FIGS. 1-10 depict various features and uses of embodiments of the present disclosure, which embodiments are generally directed to a system that can utilize an optical camera, preferably an HD or similar real-time camera, to capture an image of the specimen/sample concurrently with the acquisition of an x-ray image.

The systems and methods of embodiments of the present disclosure also address unmet needs by providing 2-D x-ray imaging and tomosynthesis apparatus and techniques that include optical imaging for imaging breast specimens that overcome the shortfall of the data received from two-dimensional and tomosynthesis imaging systems alone. The aspects of embodiments of the present disclosure also enable the use of tomosynthesis to efficiently provide accurate three-dimensional imaging of a specimen in which overlapping images having differing attenuation characteristics can be obtained by applying a three-dimensional reconstruction algorithm all in an x-ray cabinet system.

As used herein, the term "computer," "computer system", or "processor" refers to any suitable device operable to accept input, process the input according to predefined rules, and produce output, including, for example, a server, workstation, personal computer, network computer, wireless telephone, personal digital assistant, one or more microprocessors within these or other devices, or any other suitable processing device with accessible memory.

The term "computer program" or "software" refers to any non-transitory machine-readable instructions, program or library of routines capable of executing on a computer or computer system including computer readable program code.

Digital breast specimen tomosynthesis is disclosed in U.S. Pat. No. 2015/0131773 (U.S. Pat. No. 9,138,193), Lowe, et al., entitled "SPECIMEN RADIOGRAPHY WITH TOMOSYNTHESIS IN A CABINET," the disclosure of which is hereby incorporated by reference in its entirety.

The terms "camera" or "optical camera" refer to an instrument, including an optical instrument for capturing images in black and white, gray scale or color (preferably color) using reflected and/or emitted wavelengths of the electromagnetic spectrum, for example, visible light or fluorescent light, from an object, similar to a photograph or that which could be viewed by a human eye, using an electronic light-sensitive sensor array. These terms may include such instruments producing images in standard resolution or HD as well as a digital camera that can directly capture and store an image in computer-readable form using an array of electronic light-sensitive elements—typically semiconductor photo-sensors—that produce a light-intensity-dependent electronic signal in response to being illuminated.

Reference will now be made to figures wherein like structures will be provided with like reference designations. It is understood that the drawings are diagrammatic and schematic representations of exemplary embodiments of the disclosure and are not limiting of the present disclosure nor are they necessarily drawn to scale.

Specimen tomography is a three-dimensional specimen imaging system. It involves acquiring images of a sample at multiple viewpoints, typically over an arc or linear path. The three-dimensional image is constructed by the reconstruction of the multiple image data set.

One embodiment of a system 100 incorporating aspects of the present disclosure is illustrated in FIG. 1 The system 100 is totally enclosed or housed in an X-ray cabinet 22. In accordance with the aspects of the disclosed embodiments, the X-ray source 10 moves around the stationary sample, 18, typically, but not necessarily, in an arc. References 12, 14, and 16 of FIG. 1 illustrate exemplary positions of the X-ray source 10 within the X-ray cabinet 22. The reference "C" at each of the positions 12, 14, 16 of the X-ray source 10 in FIG. 1 refers to the point source of the X-ray beam. The reference "M" refers to the spread or fan of the X-ray beam.

While the detector 20 may move or rotate, in accordance with one aspect of the present disclosure, the detector 20 remains stationary relative to the sample 18 and X-ray source 10 to maintain an equidistant center point. The X-ray data taken at each of a number of exemplary positions 12, 14, 16 of the X-ray source 10 relative to the sample 18 within the X-ray cabinet 22 is processed to form images, where two or more of the differing image positions are utilized to form a digital tomosynthesis image.

In one embodiment, the aspects of the present disclosure limit the arc or linear travel of the x-ray source 10 over about a 20° to about a 50° arc, preferable about 30°, more preferable 20°. The movement can be clockwise or counter clockwise along a path, which includes for example, one or more, or a combination thereof, of the following exemplary ranges: between approximately 350° (reference position 12) to 0° (reference position 14) to 10° (reference position 16), or between approximately 340° (reference position 12) to 0° (reference position 14) to 20° (reference position 16) and or between approximately 335° (reference position 12) to 0° (reference position 14) to 25° (reference position 16). The ranges recited herein are intended to be approximate and inclusive of start and endpoints. In the example of FIG. 1 the detector 20 is stationary as is the sample 18. The sample 18 also referred to as the "object" or "imaging object" is disposed on or rests on the specimen platform 19 (which is a protective cover 21) or other surface of the detector 20.

In operation, x-ray source 10 is energized to emit an x-ray beam, generally throughout its travel along one or more of the paths or positions described above. The x-ray beam travels through the sample 18 to the detector 20 and the multiple images collected at varying angles are stored and then utilized for the tomosynthesis reconstruction. The X-ray source 10 may range from about 0 kVp to about 90 kVp, preferably a 50 kVp 1000 µa X-ray source.

Different embodiments of the present disclosure can utilize different ranges of motion of one or more of the X-ray source 10 and detector 20 as well as changing the angularity of one or both. The inventive aspects of the present disclosure differ from the prior art in that in prior art systems either the detector and X-ray source 10 and/or the isocenter 23 is above the sample and not at the detector surface. In accordance with the aspects of the present disclosure, in one embodiment, the X-ray source 10 is configured to move, as described herein, while the detector is configured to remain stationary or in a fixed position.

The detector 20 and associated electronics generate image data in digital form for each pixel at each of the angular positions, 12, 14, 16 of X-ray source 10 and translations positions of the detector 20 relative to the sample or specimen 18. While only three positions 12, 14, 16 are illustrated in FIG. 1, in practice more images are taken at differing angles. For example, in one embodiment, images can be taken at approximately every 1° of rotation or motion of x-ray source 10. The camera 30 represented in the figure may capture an optical image, preferably an HD image of the sample which can be stored with the radiographic images in computer 470.

Figure 2:
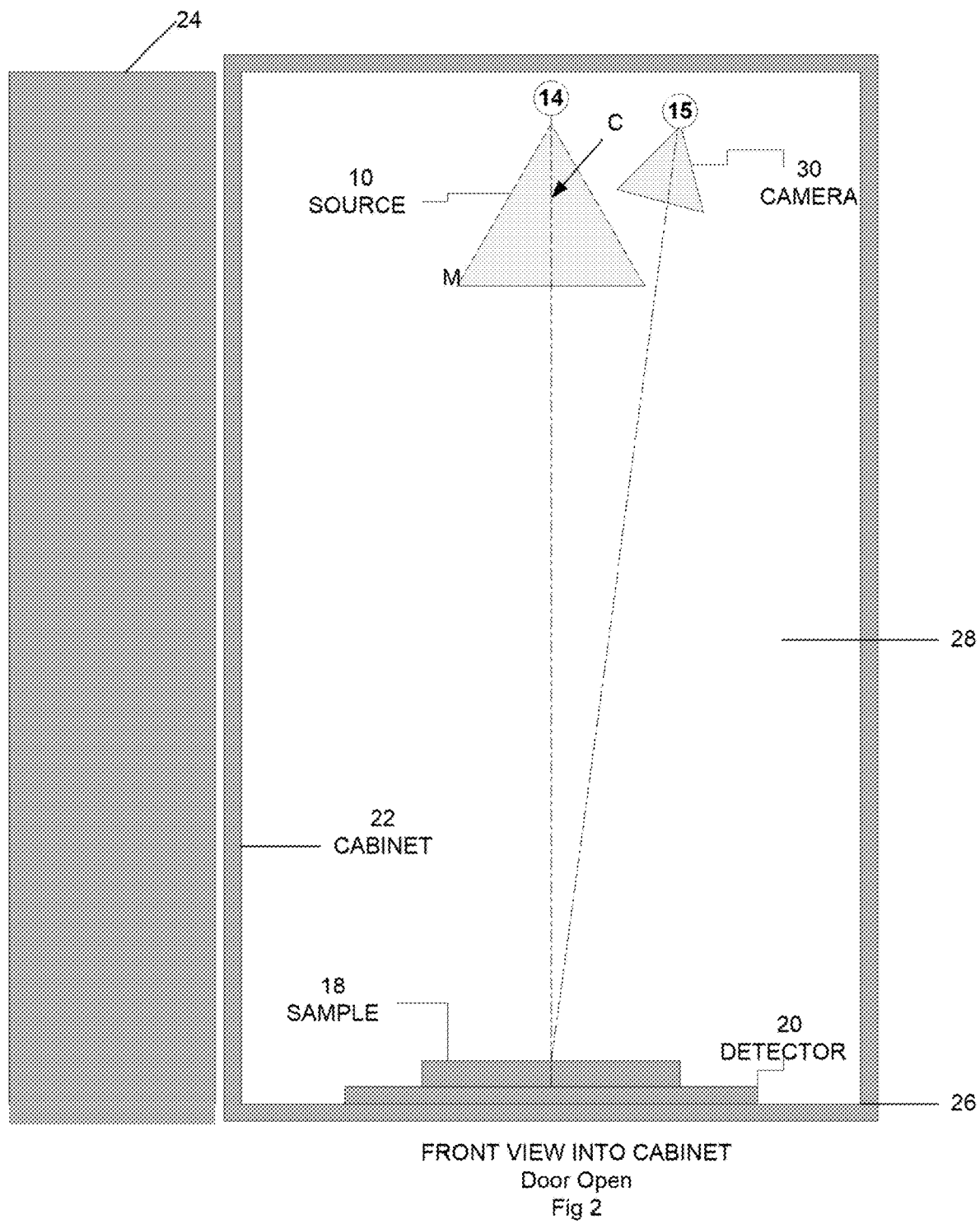
FIG. 2—Schematically illustrates an exemplary orientation of the X-ray source, specimen, and digital detector as viewed when the door of the cabinet is open, in one embodiment of a system incorporating aspects of the present disclosure.

FIG. 2 schematically illustrates one embodiment of the orientation of the X-ray source 10 as seen when the door 24 is opened and the X-ray source 10 is locate at approximately 0°, reference point 14 in this example, within the X-ray cabinet 22. In this embodiment, the motion of the X-ray source 10 can generally occur from the back to the front of the X-ray cabinet 22 with the detector 20 oriented, or otherwise disposed, at the base 26 of the X-ray cabinet 22, within the X-ray cabinet chamber 28. In one embodiment, the detector 20 is suitably coupled to the base 26 of the X-ray cabinet 22. The X-ray spread in this example can be from about 0 kVp to about 50 kVp with the system 100 preferably utilizing an AEC (Automatic Exposure Control) to ascertain the optimal setting to image the object or sample 18 being examined.

In one embodiment, the detector 20, X-ray source 10, and the swing arm 60 (FIG. 5) servo mechanism are controlled via a combination of one or more of software and hardware, such as non-transitory machine-readable instructions stored in a memory that are executable by one or more processors. On example of such a configuration can include controller cards of a computer 470 (FIG. 4), such as a MS Windows based computer. In one embodiment, non-transitory machine readable instructions being executed by one or more processors of the computer 470 is utilized to compile data received from the detector 20 and present resulting images to a suitable display or monitor 472 (FIG. 4) at each imaging position, such as positions 12, 14 and 16 shown in FIG. 1, the detector 20 generates the respective digital values for the pixels in a two-dimensional array. The size of detector 20 may range, for example, from about 5.08 centimeters by 5.08 centimeters to about 40.64 centimeters by 40.64 centimeters, preferably about 12.7 centimeters by 15.24 centimeters. In one example, detector 20 has a rectangular array of approximately 1536×1944 pixels with a pixel size of 74.8 micrometers. The image dataset attained at each respective position may be processed either at the full spatial resolution of detector 20 or at a lower spatial resolution by overlapping or binning a specified number of pixels in a single combined pixel value.

For example, if we bin at a 2×2 ratio, then there would be an effective spatial resolution of approximately 149.6 micrometers. This binning may be achieved within the original programming of the detector 20 or within the computer 470 providing the tomosynthetic compilation and image.

Figure 3:
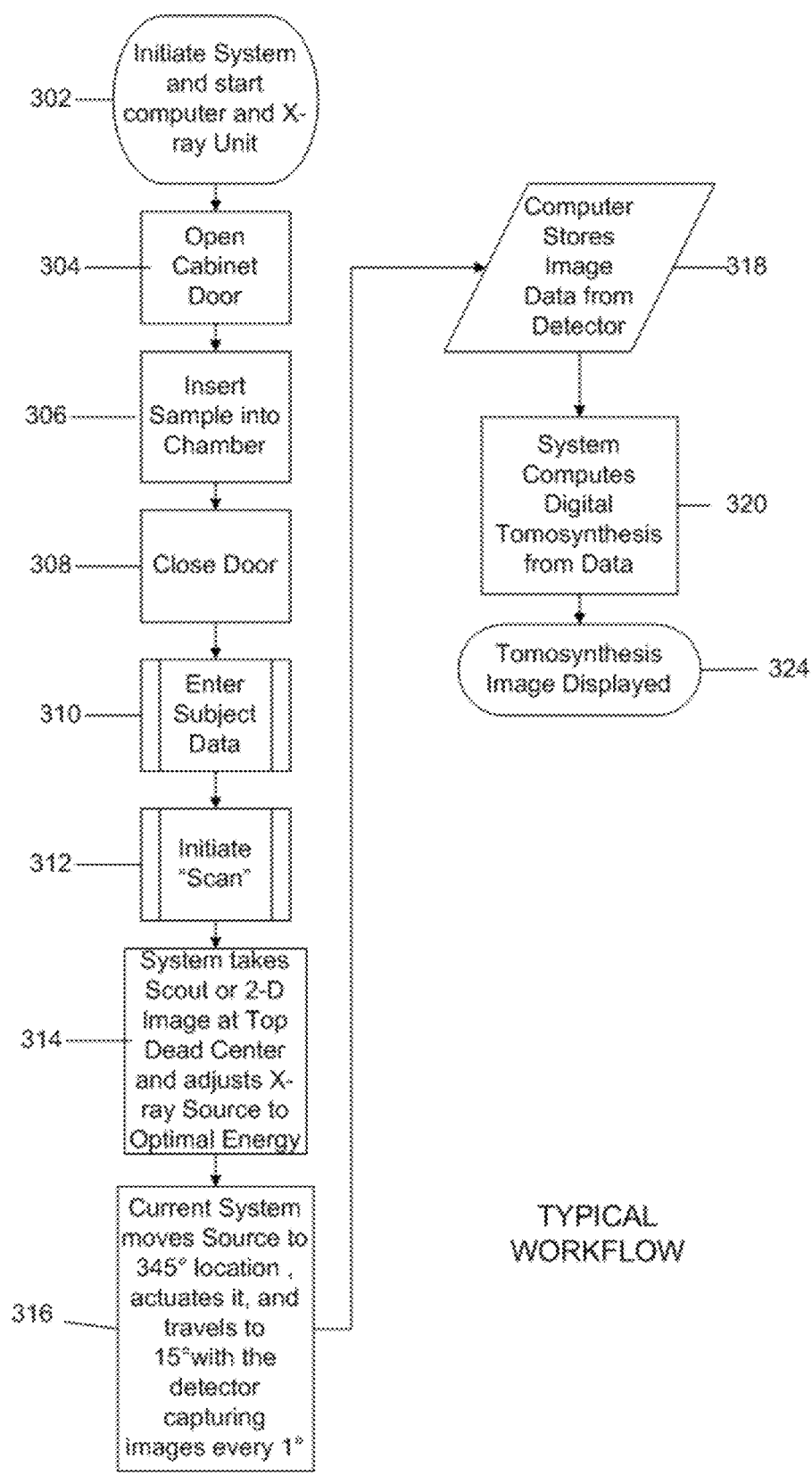
FIG. 3—Displays an exemplary workflow/flowchart of an aspect of the disclosed embodiments.

FIG. 3 illustrates one embodiment of an exemplary workflow from initiating 302 the system 100 through imaging, reconstruction and display 324 of data images collected of the sample 18.

As will be generally understood, the system 100 is initiated 302, the X-ray cabinet door 24 opened 304, and the sample 18 placed into 306 the X-ray cabinet chamber 28. As shown in FIG. 2, for example, the sample 18 is positioned on the detector 20 in a suitable manner. The door 24 is closed 308.

The data and information regarding the sample 18, including any other suitable information or settings relevant to the imaging process and procedure, is entered 310 into the computer 470. The scan is initiated 312. The system 100 will take 314 scout or 2-D images at Top Dead Center, which for purposes of this example is position 14 of FIGS. 1 and 2. The X-ray source 10 can then be moved to other positions, such as positions 12 and 16, and the detector 20 can be used to capture 316 images at various increments along the travel path of the X-ray source 10, such as about every 1 degree.

The captured images are stored 318 and digital tomosynthesis is performed 320. The tomosynthesis image is then displayed 324.

Other embodiments of a system 100 incorporating aspects of the present disclosure are illustrated in FIGS. 1 and 2 where system 100 is totally enclosed or housed in an x-ray cabinet 22 and the x-ray source 10 is stationary relative to the stationary sample 18 and can be used to obtain a 2-D image. In these embodiments, x-ray source 10 can be positioned at position 14 and the reference "C" refers to the point source of the x-ray beam and the reference "M" refers to the spread or fan of the x-ray beam. While the detector 20 may move or rotate, in accordance with one aspect of the present disclosure, the detector 20 can remain stationary relative to the sample 18 and x-ray source 10 to maintain an equidistant center point. The sample 18 also referred to as the "object" or "imaging object" may be disposed on or rest on the specimen platform 19 (which is a protective cover) or other surface of the detector 20. As with the previous embodiments described herein, the inventive aspects of the present disclosure differ from the prior art in that in prior art systems either the detector and x-ray source 10 and/or the isocenter is above the sample and not at the detector surface. In operation, source 10 is energized to emit an x-ray beam at position 14, located at approximately 0°, and thereby obtain a 2-D image of sample 18. In operation, x-ray source 10 is energized to emit an x-ray beam, generally throughout its travel along one or more of the paths or positions described above. The x-ray beam travels through the sample 18 to the detector 20 and a 2-D image is stored. The x-ray source 10 may range from about 0 kVp to about 90 kVp, preferably a 50 kVp 1000 μa x-ray source.

Figure 4:
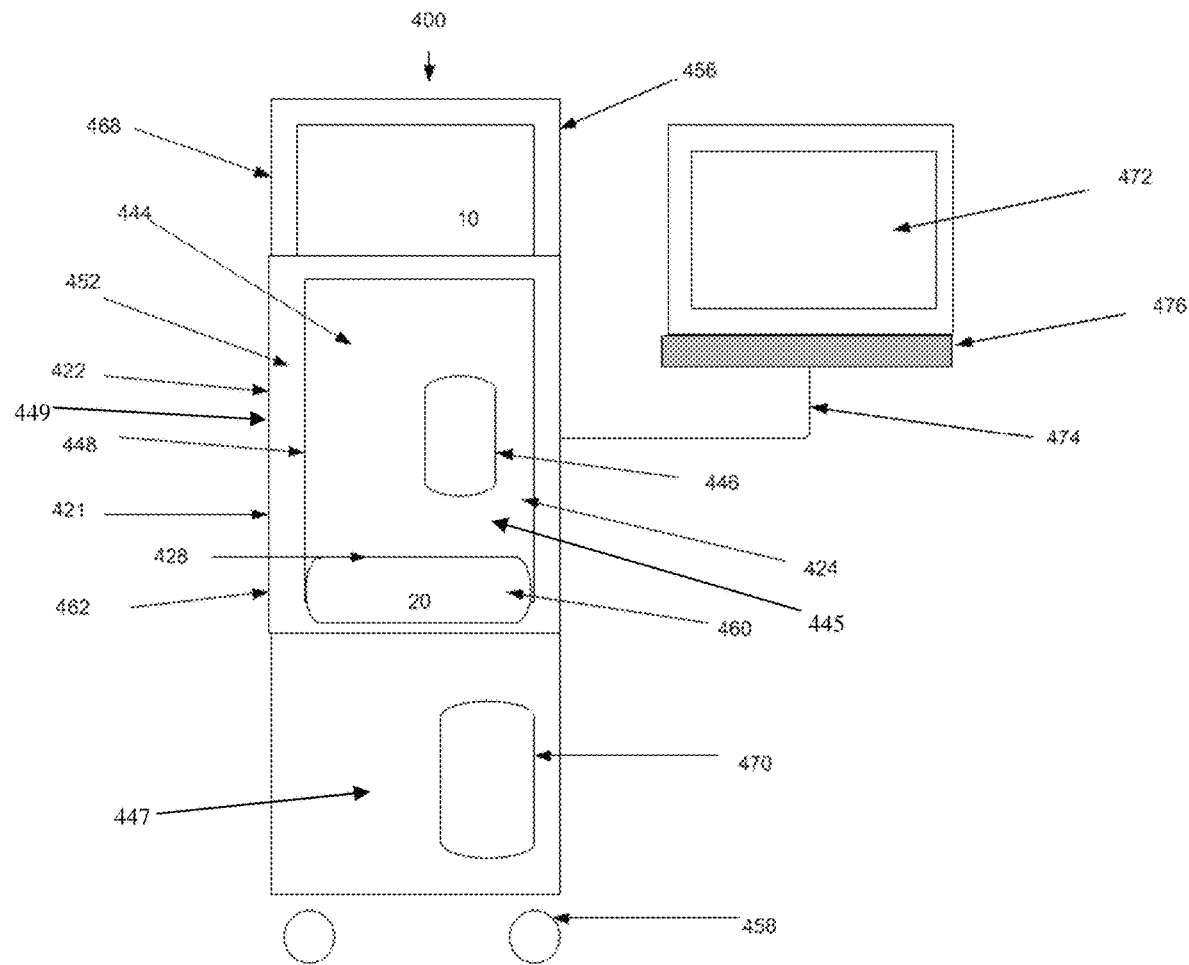
FIG. 4—Displays an example of an X-ray Cabinet System incorporating aspects of the present disclosure.

FIG. 4 shows one embodiment of an X-ray Cabinet System 400 incorporating aspects of the present disclosure. In this embodiment, the X-ray Cabinet System 400 is mounted on wheels 458 to allow easy portability. In alternate embodiments, the X-ray Cabinet System 400 can be mounted on any suitable base or transport mechanism. The cabinet 422 in this example, similar to the exemplary X-ray cabinet 22 of FIG. 1, is constructed of a suitable material such as steel. In one embodiment, the cabinet 422 comprises painted steel defining a walled enclosure 449 with an opening in cabinet chamber 428. Within the cabinet chamber 428, behind door 424, resides an interior space or chamber 445 forming a sample chamber 444, which in this example is constructed of stainless steel. Access to the sample chamber 444 is via an opening 446. In one embodiment, the opening 446 of the sample chamber 444 has a suitable door or cover, such as a moveable cover 448. In one embodiment, the moveable cover 448 comprises a door which has a window of leaded glass.

Between the outer wall 421 of cabinet 422 and the sample chamber 444 are sheets of lead 452 that serve as shielding to reduce radiation leakage emitted from the X-ray source 10. In the example of FIG. 4, the X-ray source 10 is located in the upper part 456 of the cabinet 422, in the source enclosure 468. The detector 20 is housed in the detector enclosure 460 at an approximate midpoint 462 of the cabinet 422.

Figure 5:
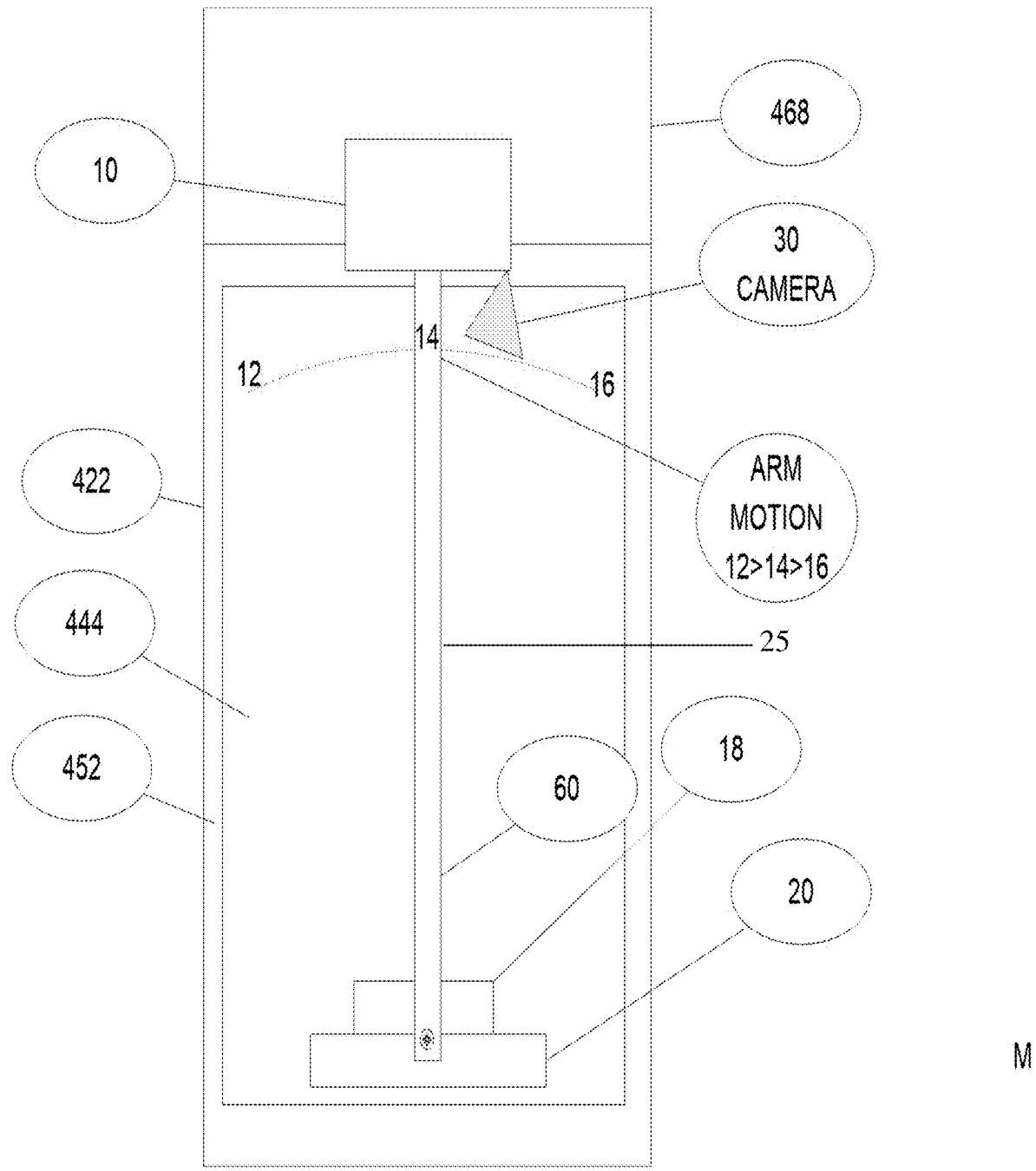
FIG. 5—Displays the sample chamber of the embodiment of FIG. 4 with the swing arm and a detector.
Figure 6:
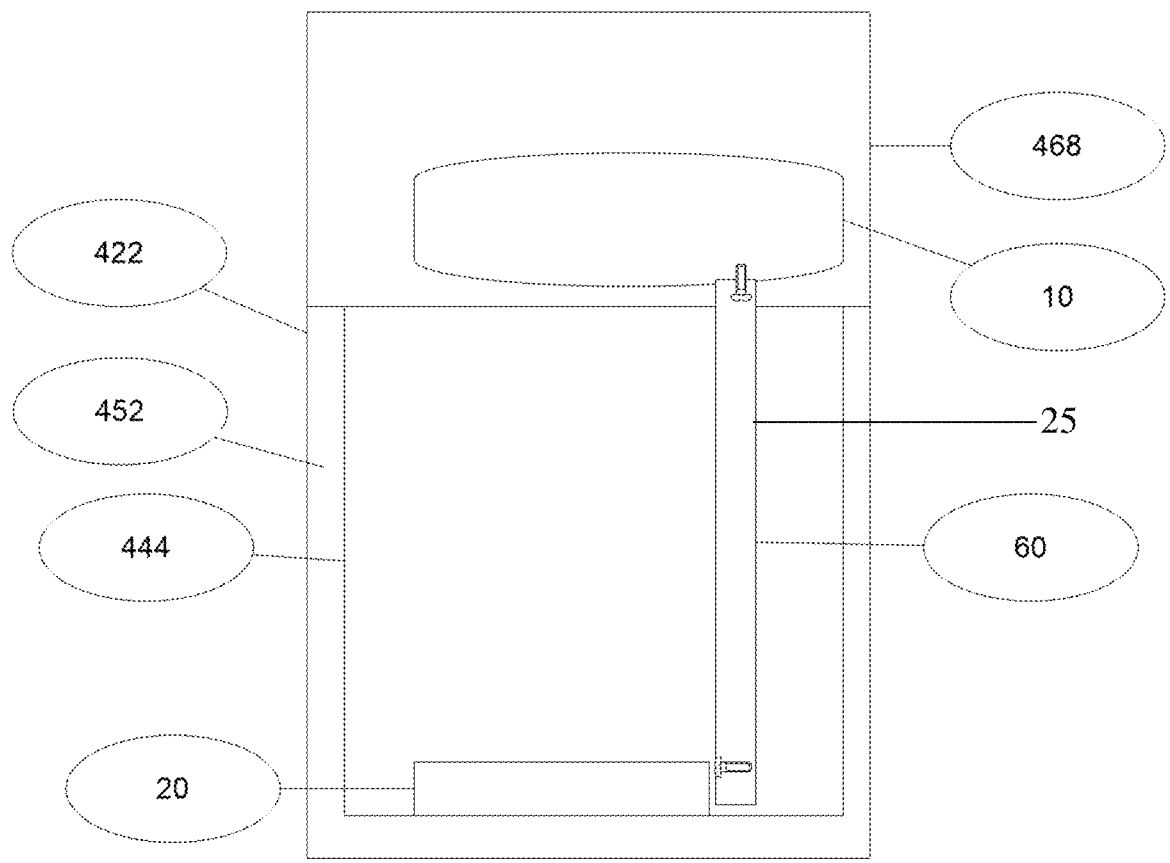
FIG. 6—Displays the lateral view of the X-ray source of the embodiment of FIG. 4 mounted to the top of the swing arm.

In one embodiment, a controller or computer 470 in equipment enclosure 447 controls the collection of data from the detector 20, controls a motion control mechanism 25, for example, the swing arm 60 shown in FIGS. 5 & 6, and X-ray source 10. A monitor 472 displays the compiled data and can, for example, be mounted on an articulating arm 474 that is attached to the cabinet 422. The computer 470 receives commands and other input information entered by the operator via a user interface 476, such as a keyboard and mouse for example. In one embodiment, the computer 470 can comprise a touch screen or near touch screen device. Although the aspects of the disclosed embodiments will generally be described with respect to a computer 470, it will be understood that the computer 470 can comprise any suitable controller or computing device. Such computing devices can include, but are not limited to, laptop computers, mini computers, tablets and pad devices.

The computer 470 can be configured to communicate with the components of the X-ray cabinet system 400 in any suitable manner, including hardwired and wireless communication. In one embodiment, the computer 470 can be configured to communicate over a network, such as a Local Area Network or the Internet.

FIG. 5 shows a front interior view and FIG. 6 shows a lateral interior view of the sample chamber of imaging unit cabinet of FIG. 4. In this embodiment, a sample 18 is placed or otherwise disposed onto the detector 20. Using the computer 470 shown in FIG. 4, the operator enters in the parameters for the scan via the user interface 476, which can be displayed on the monitor 472. As used herein, the term "display" or "monitor" means any type of device adapted to display information, including without limitation CRTs, LCDs, TFTs, plasma displays, LEDs, and fluorescent devices. The computer 470 then sends the appropriate commands to the X-ray source 10 and detector 20 to activate image collection while the swing arm 60 is moving along a path or arc from position 14 to 12 to 16 (which are shown in FIGS. 1 and 5) or vice versa as described, which in this embodiment are at 345°, 0°, and 15° respectively with 0° at top dead center. At the end of the travel of the swing arm 60 at either position 12 or 16, the computer 470 issues the command to the X-ray source 10 and the detector 20 to cease operating. The individual 2-dimensional (2-D) images which were collected, in this example at 1° increments, are then tabulated in the computer 470 to create the tomosynthetic images. In one embodiment, the operator may select which images they wish via the user interface 476 as they are being displayed on the monitor 472. In one embodiment, the devices and components of the X-ray cabinet system 400 are suitably communicatively coupled together, including one or more of hard wire connections or wireless connections using a suitable wireless connection and communication transmission protocol, as will generally be understood. The X-ray cabinet system 400 can also be configured to transfer images via USB, CD-ROM, or WIFI.

The dynamic imaging software of the disclosed embodiments reconstructs three-dimensional images (tomosynthesis) from two-dimensional projection images in real-time and on-demand. The software offers the ability to examine any slice depth, tilt the reconstruction plane for multiplanar views and gives higher resolution magnifications. FIGS. 7A, 7B, and 7C illustrate exemplary images of an apple using the above process.

FIG. 7A is an image of a slice of the apple at it's very top. 59 mm from the bottom. FIG. 7B is an image of an apple computed at 30.5 mm up from the detector, and FIG. 7C is a view of the apple computed at 13.5 mm from the bottom.

The real-time image reconstruction of the present disclosure enables immediate review, higher throughput, and more efficient interventional procedures reducing patient call backs and data storage needs. Multiplanar reconstruction enables reconstruction to any depth, magnification and plane, giving the viewer the greater ability to view and interrogate image data, thereby reducing the likelihood of missing small structures. Built-in filters allow higher in plane resolution and image quality during magnification for greater diagnostic confidence. Software is optimized for performance using GPU Technology.

The reconstruction software used in conjunction with the aspects of the present disclosure provides the users greater flexibility and improved visibility of the image data. It reconstructs images at any depth specified by the user rather than at fixed slice increments. With fixed slice increments, an object located between two reconstructed slices, such as a calcification, is blurred and can be potentially missed. The aspects of the present disclosure provide for positioning the reconstruction plane so that any object is exactly in focus. This includes objects that are oriented at an angle to the detector 20. The aspects of the present disclosure provide for the reconstruction plane to be angled with respect to the detector plane.

Figure 8:
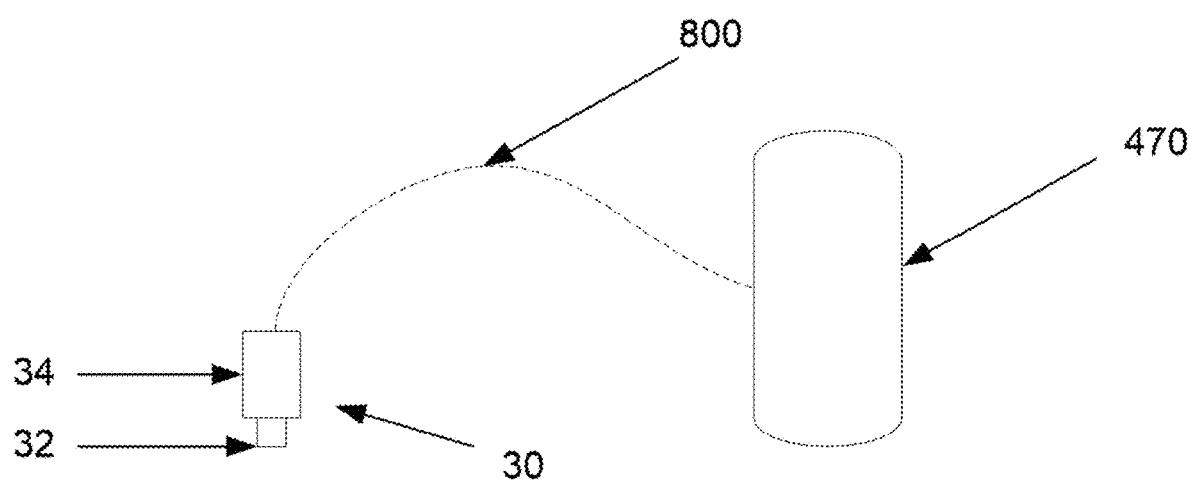
FIG. 8—Displays an interconnection diagram of an HD camera embodiment that may be utilized in aspects of the disclosed embodiments of the present disclosure.
Figure 9:
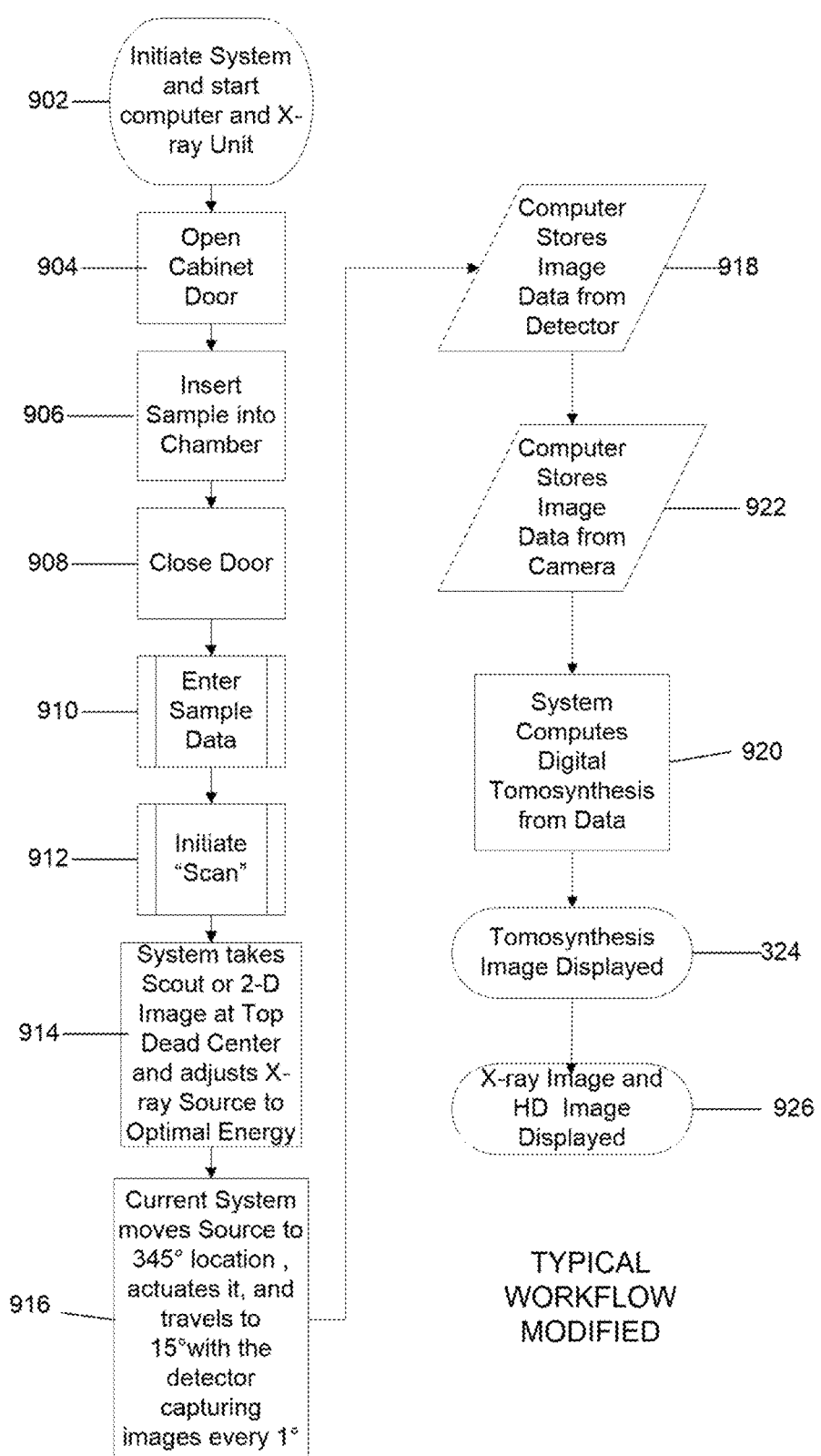
FIG. 9—Displays an exemplary modified workflow/flowchart of an aspect of the disclosed embodiments.

FIGS. 8-10 depict various features of embodiments of the present disclosure, which embodiments are generally directed to a system that can utilize an optical camera, preferably a real-time camera, to capture a visual image of a specimen/sample concurrently or at substantially the same time as the acquisition of an x-ray image. Referring to FIG. 8, there is shown the interconnection of an embodiment of a camera 30 incorporated into a Cabinet X-Ray Unit which connects to and can be controlled by the computer 470 via cable 800 including, for example a USB cable. Other wireless formats for communication between camera 30 and computer 470 can also be used in embodiment of the present disclosure. Camera 30 may include an optical lens assembly 32 through which an optical image passes and is focused upon an electronic light-sensitive sensory array included in the camera body 34. The optical image can then be sent using an electronic signal from the sensory array to the computer 470 via cable 800 or other wireless formats. The optical image as well as a 2-D x-ray image or tomosynthesis image can also be stored in the computer 470 for future examination and viewing, including storage in memory (e.g., RAM) or a disc recording medium (e.g., CD, DVD, etc.)

Camera 30 is included in FIGS. 1, 2 and 5 as well showing embodiments in camera 30, for example, located at position 15 in the cabinet x-ray unit such that it is capable of capturing a visual image of sample 18 in cabinet 22 and x-ray cabinet chamber 28 in FIGS. 1 and 2 and in cabinet 422 and sample chamber 444 in FIG. 5, preferably such that the optical image captured by camera and the x-ray image (2-D x-ray image or tomosynthetic x-ray image) show the sample or specimen at substantially, preferably exactly, the same orientation for the optical and x-ray images. In one embodiment, a medical professional or other authorized operator places a specimen/sample into the chamber, closes and secures the door, and presses, for example, the "acquire" command on the system using, for example, a keyboard or touch screen monitor that can be used to enter system commands or other information. In one embodiment, pressing this command can simultaneously or in substantially close proximity in time, the computer commands the optical camera and x-ray source in conjunction with the x-ray detector to capture images from both sources, the latter being an x-ray image or series of images from which tomosynthetic images can be assemble. In another embodiment, as a result of pressing this command, the x-ray source in conjunction with the x-ray detector captures an x-ray image or series of images from which tomosynthetic images can be assemble. The resulting x-ray image or tomosynthetic image can them be displayed at the same time as a real-time optical image is captured through the camera.

In the systems and methods included in this disclosure as well as the embodiments disclosed herein, the resulting x-ray generated and optical camera images can be displayed each alone or together as overlaid together, adjacent or PIP (Picture-in-Picture) on the monitor FIGS. 4—472. This, in turn, provides more flexibility for a clinician or other user of the system and simplifies the procedure. The separate images from the camera and x-ray detector separately as well as the tomosynthetic, overlaid, adjacent and PIP images can be stored in the computer hard drive on the system 470 or a separate memory device, such as for example, a separate hard drive, flash drive, CD-ROM, DVD, etc. for future analysis. The camera can capture a visible light or other electromagnetic wavelength reflected or emitted by the sample or portions thereof, for example, though the use of fluorescent or other markers using a suitable light source where required. Manual input for operation of the cabinet x-ray unit may be initiated via keyboard or monitor touch screen and the resulting image from both the manual-initiated examination can be displayed on the screen and configured in accordance with one example embodiment of the present disclosure.

FIG. 9 illustrates one embodiment of a modified basic workflow of the cabinet x-ray unit with the addition of the storage of the image data 922 and the combination x-ray image and HD image displayed 926.

As will be generally understood, the system 100 is initiated 902, the X-ray cabinet door 24 opened 904, and the sample 18 placed into 906 the X-ray cabinet chamber 28. As shown in FIG. 2, for example, the sample 18 is positioned on the detector 20 in a suitable manner. The door 24 is closed 908.

The data and information regarding the sample 18, including any other suitable information or settings relevant to the imaging process and procedure, is entered 910 into the computer 470. The scan is initiated 912. The system 100 will take 914 scout or 2-D images at Top Dead Center, which for purposes of this example is position 14 of FIGS. 1 and 2. The X-ray source 10 can then be moved to other positions, such as positions 12 and 16, and the detector 20 can be used to capture 916 images at various increments along the travel path of the X-ray source 10, such as about every 1 degree. An optical image, for example, an HD image, is captured by the camera and stored in the computer 922. The captured images are stored 918 and digital tomosynthesis is performed 920. The tomosynthesis image is then displayed 924. The combination x-ray image and HD image are then displayed 926, the x-ray image can be either the 2-D image from 914 or the tomosynthesis image from 920. Another embodiment of the workflow embodiment illustrated in FIG. 9 can include obtaining a 2-D x-ray image as in 914 without the detector 20 being used to capture 916 images at various increments along the travel path and related steps 920 and 924 related to tomosynthesis FIG. 10A exhibits the HD image of a breast specimen and FIG. 10B exhibits the x-ray image of the specimen showing the actual placement of the markers 1002 and orientation of the specimen as well as placement of the markers 1002 within the breast specimen 1000. Markers 1002 are utilized to delineate the outer boundaries of the suspect area that needs to be excised in the X, Y, and Z directions. The markers may include radioactive seeds, coils, wires, and/or radiopaque/visible items which are implanted before the surgery by an interventional radiologist prior to the surgery and are utilized to denote boundaries of the region of interest.

Indeed, it is appreciated that the system and its individual components can include additional features and components, though not disclosed herein, while still preserving the principles of the present disclosure. Note also that the base computer can be one of any number devices, including a desktop or laptop computer, etc.

Aspects of the present disclosure may be embodied in other specific forms without departing from its spirit or essential characteristics. The described embodiments are to be considered in all respects only as illustrative, not restrictive. All changes that come within the meaning and range of equivalency of the claims are to be embraced within their scope.

What is claimed is:

1. A cabinet x-ray and optical camera system for obtaining x-ray images and optical images of a specimen, the cabinet x-ray and optical camera system comprising:
   a cabinet defining an interior chamber;
   a display;
   an x-ray system including:
      an x-ray source;
      a digital x-ray detector; and
      a specimen platform;
   a high-definition optical camera configured to capture an optical image of the specimen; and
   a controller configured to:
      selectively energize the x-ray source to emit x-rays through the specimen to the digital x-ray detector;
      control the digital x-ray detector to collect a projection x-ray image of the specimen when the x-ray source is energized;
      selectively display the projection x-ray image on the display;
      control the high-definition digital optical camera to capture and collect an optical image of the specimen; and
      selectively display the optical image on the display.

2. The cabinet x-ray and optical camera system of claim 1, wherein the cabinet comprises a walled enclosure surrounding the interior chamber, a door configured to cover the interior chamber, and a sampling chamber within the interior chamber, for containing the specimen.

3. The cabinet x-ray and optical camera system of claim 1, wherein the specimen platform is configured for excised tissue, organ, or bone specimens.

4. The cabinet x-ray and optical camera system of claim 1, wherein the specimen platform is configured for any organic or inorganic specimen that fits inside the interior chamber.

5. The cabinet x-ray and optical camera system of claim 1, wherein
   the specimen platform comprises a protective cover, which is in physical contact with the digital x-ray detector;
   wherein the x-ray system further comprises:
   a motion control mechanism configured for moving the x-ray source to or along a plurality of positions within the interior chamber relative to the specimen disposed on the specimen platform; and wherein the controller further configured to:
selectively energize the x-ray source to emit x-rays through the specimen to the digital x-ray detector at selected positions of the x-ray source relative to the specimen such that an isocenter of the emitted x-rays at the selected positions is located at a surface of the digital x-ray detector;
control the digital x-ray detector to collect the projection x-ray images of the specimen when the x-ray source is energized at the selected positions, wherein one of the projection x-ray images is a two-dimensional x-ray image taken at standard imaging angle of approximately 0°;
create a tomosynthetic x-ray image reconstructed from a collection of projection x-ray images;
process the collection of the projection x-ray images in the controller to create one or more reconstructed tomosynthetic x-ray images representing a volume of the specimen and relating to one or more image planes that are selectively the same or different from that of the two-dimensional x-ray image; and
selectively display the two-dimensional x-ray image and the one or more reconstructed tomosynthetic x-ray images.

6. The cabinet x-ray and optical camera system of claim 1, wherein the controller is configured to control the digital x-ray detector to collect a projection x-ray image of the specimen when the x-ray source is energized, and control the high-definition digital optical camera to capture and collect the optical image of the specimen such that the projection x-ray image and the optical image are collected at substantially the same time.

7. The cabinet x-ray and optical camera system of claim 1, wherein an orientation of the specimen in the projection x-ray image and the optical image are substantially the same.

8. The cabinet x-ray and optical camera system of claim 1, wherein the controller is configured to selectively display the projection x-ray image and the optical image on the display simultaneously side-by-side or picture-in-a-picture.

9. The cabinet x-ray and optical camera system of claim 1, wherein the controller is configured to selectively display the projection x-ray image and the optical image on the display overlaid.

10. The cabinet x-ray and optical camera system of claim 1, wherein the high-definition digital optical camera is configured to capture a real-time image of the specimen, and the controller is configured to control the high-definition digital optical camera to capture and collect a real-time optical image of the specimen; and selectively display the real-time optical image on the display.

11. A cabinet x-ray and optical camera system for obtaining x-ray images, projection x-ray images, reconstructed tomosynthetic x-ray images, and optical images of a specimen, the cabinet x-ray and optical camera system comprising:
a cabinet defining an interior chamber and an equipment enclosure;
a display;
an x-ray system including:
an x-ray source positioned in the interior chamber;
a digital x-ray detector positioned in the interior chamber;
a specimen platform positioned in the interior chamber, and wherein the specimen platform comprises a protective cover, which is in physical contact with the digital x-ray detector; and
a motion control mechanism positioned in the interior chamber and configured for moving the x-ray source to or along a plurality of positions within the interior chamber relative to the specimen disposed on the specimen platform;
a high-definition digital optical camera positioned in the interior chamber configured to capture an optical image of the specimen; and
a controller positioned in the equipment enclosure and configured to:
selectively energize the x-ray source to emit x-rays through the specimen to the digital x-ray detector at selected positions of the x-ray source relative to the specimen such that an isocenter of the emitted x-rays at the selected positions is located at a surface of the digital x-ray detector;
control the digital x-ray detector to collect projection x-ray images of the specimen when the x-ray source is energized at the selected positions, wherein one of the projection x-ray images is a two-dimensional x-ray image taken at standard imaging angle of approximately 0°;
create a tomosynthetic x-ray image reconstructed from a collection of the projection x-ray images;
process the collection of the projection x-ray images in the controller to create one or more reconstructed tomosynthetic x-ray images representing a volume of the specimen and relating to one or more image planes that are selectively the same or different from that of the two-dimensional x-ray image;
control the high-definition digital optical camera to capture and collect an optical image of the specimen; and
selectively display at least one of the two-dimensional x-ray image, the one or more reconstructed tomosynthetic x-ray images, and the optical image on the display.

12. The cabinet x-ray and optical camera system of claim 11, wherein the cabinet comprises a walled enclosure surrounding the interior chamber, a door configured to cover the interior chamber, and a sampling chamber within the interior chamber for containing the specimen.

13. The cabinet x-ray and optical camera system of claim 11, wherein the specimen platform is configured for excised tissue, organ, or bone specimens.

14. The cabinet x-ray and optical camera system of claim 11, wherein the specimen platform is configured for any organic or inorganic specimen that fits inside the interior chamber.

15. The cabinet x-ray and optical camera system of claim 11, wherein the controller is configured to control the digital x-ray detector to collect projection x-ray images of the specimen when the x-ray source is energized, and control the high-definition digital optical camera to capture and collect the optical image of the specimen such that the optical image is collected at substantially the same time as at least one of the projection x-ray images.

16. The cabinet x-ray and optical camera system of claim 11, wherein an orientation of the specimen in the two-dimensional x-ray image, the one or more reconstructed tomosynthetic x-ray images, and the optical image are substantially the same.

17. The cabinet x-ray and optical camera system of claim 11, wherein the high-definition digital optical camera is configured to capture a real-time image of the specimen, and the controller is configured to control the high-definition digital optical camera to capture and collect a real-time optical image of the specimen; and selectively display the real-time optical image on the display.

18. A method for obtaining a projection x-ray image and an optical image of a specimen in a cabinet x-ray and optical image system, processing and displaying the projection x-ray image and the optical image of the specimen, wherein the cabinet x-ray and optical image system comprises:
  a cabinet defining an interior chamber;
  a display;
  an x-ray system including:
    an x-ray source;
    a digital x-ray detector; and
    a specimen platform;
  a high-definition digital optical camera configured to capture an optical image of the specimen; and
  a controller configured to:
    selectively energize the x-ray source to emit x-rays through the specimen to the digital x-ray detector;
    control the digital x-ray detector to collect a projection x-ray image of the specimen when the x-ray source is energized;
    selectively display the projection x-ray image on the display;
    control the high-definition digital optical camera to capture and collect an optical image of the specimen; and
    selectively display the optical image on the display;
  wherein the method comprises:
    controlling the digital x-ray detector to collect a projection x-ray image of the specimen when the x-ray source is energized;
    controlling the high-definition digital optical camera to capture and collect an optical image of the specimen; and
    selectively displaying at least one of the projection x-ray image and the optical image on the display.

19. The method of claim 18, further comprising displaying the projection x-ray image and the optical image simultaneously side-by-side or picture-in-a-picture.

20. The method of claim 18, further comprising displaying the projection x-ray image and the optical image on the display overlaid.

21. The method of claim 18, wherein
  the specimen platform comprises a protective cover, which is in physical contact with the digital x-ray detector;
  wherein the x-ray system further comprises:
  a motion control mechanism configured for moving the x-ray source to or along a plurality of positions within the interior chamber relative to the specimen disposed on the specimen platform; and
  a controller further configured to:
    selectively energize the x-ray source to emit x-rays through the specimen to the digital x-ray detector at selected positions of the x-ray source relative to the specimen such that an isocenter of the emitted x-rays at the selected positions is located at a surface of the digital x-ray detector;
    control the digital x-ray detector to collect projection x-ray images of the specimen when the x-ray source is energized at the selected positions, wherein one of the projection x-ray images is a two-dimensional x-ray image taken at standard imaging angle of approximately 0°;
    create a tomosynthetic x-ray image reconstructed from a collection of the projection x-ray images;
    process the collection of the projection x-ray images in the controller to create one or more reconstructed tomosynthetic x-ray images representing a volume of the specimen and relating to one or more image planes that are selectively the same or different from that of the two-dimensional x-ray image; and
    selectively display the two-dimensional x-ray image and the one or more reconstructed tomosynthetic x-ray images, and
  the method further comprises:
    controlling the digital x-ray detector to collect projection x-ray images of the specimen when the x-ray source is energized at the selected positions such that the isocenter of the emitted x-rays at the selected positions is located at a surface of the digital x-ray detector, wherein one of the projection x-ray images is a two-dimensional x-ray image taken at standard imaging angle of approximately 0°;
    creating a tomosynthetic x-ray image reconstructed from a collection of the projection x-ray images;
    processing the collection of the projection x-ray images in the controller to create one or more reconstructed tomosynthetic x-ray images representing a volume of the specimen and relating to one or more image planes that are selectively the same or different from that of the two-dimensional x-ray image; and
    selectively displaying at least one of the one or more reconstructed tomosynthetic x-ray images on the display.

22. The method of claim 21, further comprising displaying at least one of the projection x-ray images or the one or more reconstructed tomosynthetic x-ray images and the optical image simultaneously side-by-side or picture-in-a-picture.

23. The method of claim 21, further comprising displaying at least one of the projection x-ray images or the one or more reconstructed tomosynthetic x-ray images and the optical image on the display overlaid.

24. The method of claim 18, wherein controlling the digital x-ray detector to collect the projection x-ray image of the specimen when the x-ray source is energized, and controlling the high-definition digital optical camera to capture and collect the optical image of the specimen such that the projection x-ray image and the optical image are collected at substantially the same time.

25. The method of claim 18, wherein the high-definition digital optical camera is configured to capture a real-time image of the specimen, and the controller is configured to control the high-definition digital optical camera to capture and collect the real-time optical image of the specimen; and selectively display a real-time optical image on the display and the method further includes controlling the high-definition digital optical camera to capture and collect a real-time optical image of the specimen; and selectively displaying the real-time optical image on the display.

26. The method of claim 18, further including identifying positions of markers in the displayed in at least one of the projection x-ray image of the specimen, the markers used to delineate outer boundaries of a suspect area of the specimen that needs to be excised, and excising the suspect area of the specimen.

* * * * *